United States Patent
Miret Carceller et al.

(10) Patent No.: US 10,130,830 B2
(45) Date of Patent: Nov. 20, 2018

(54) PRESERVATIVE SYSTEMS COMPRISING CATIONIC SURFACTANTS

(75) Inventors: Jordi Miret Carceller, Barcelona (ES); Sergi Figueras Roca, Barcelona (ES); Roger Segret Pons, Barcelona (ES)

(73) Assignee: Laboratorios Miret, S.A., Barcelona (ES)

( * ) Notice: Subject to any disclaimer, the term of this patent is extended or adjusted under 35 U.S.C. 154(b) by 2017 days.

(21) Appl. No.: 11/997,160

(22) PCT Filed: Aug. 1, 2005

(86) PCT No.: PCT/EP2005/053735
§ 371 (c)(1),
(2), (4) Date: Mar. 5, 2008

(87) PCT Pub. No.: WO2007/014580
PCT Pub. Date: Feb. 8, 2007

(65) Prior Publication Data
US 2010/0092420 A1    Apr. 15, 2010

(51) Int. Cl.
| | | |
|---|---|---|
| A61Q 19/10 | (2006.01) | |
| A23B 4/20 | (2006.01) | |
| A23B 4/24 | (2006.01) | |
| A23B 7/154 | (2006.01) | |
| A23B 7/157 | (2006.01) | |
| A23L 3/3508 | (2006.01) | |
| A23L 3/3517 | (2006.01) | |
| A23L 3/3526 | (2006.01) | |
| A23L 3/3544 | (2006.01) | |
| A23L 3/358 | (2006.01) | |
| A61K 8/44 | (2006.01) | |
| A61K 8/49 | (2006.01) | |
| A61Q 19/00 | (2006.01) | |

(52) U.S. Cl.
CPC .......... *A61Q 19/10* (2013.01); *A23B 4/20* (2013.01); *A23B 4/24* (2013.01); *A23B 7/154* (2013.01); *A23B 7/157* (2013.01); *A23L 3/3508* (2013.01); *A23L 3/358* (2013.01); *A23L 3/3517* (2013.01); *A23L 3/3526* (2013.01); *A23L 3/3544* (2013.01); *A61K 8/44* (2013.01); *A61K 8/442* (2013.01); *A61K 8/4946* (2013.01); *A61Q 19/00* (2013.01); *A61K 2800/524* (2013.01); *Y02A 40/944* (2018.01)

(58) Field of Classification Search
CPC .................................................. A01N 47/44
See application file for complete search history.

(56) References Cited

U.S. PATENT DOCUMENTS

| | | | |
|---|---|---|---|
| 3,707,505 A | | 12/1972 | Maeda et al. |
| 5,780,658 A | * | 7/1998 | Martinez-Pardo et al. .... 554/51 |
| 6,277,359 B1 | * | 8/2001 | Raths et al. ................ 424/65 |
| 7,029,698 B2 | * | 4/2006 | Waranis et al. ............ 424/451 |
| 2002/0119109 A1 | * | 8/2002 | Herpens et al. ............ 424/68 |
| 2004/0122095 A1 | | 6/2004 | Bonaventura et al. |
| 2004/0166082 A1 | | 8/2004 | Urgell-Beltran et al. |
| 2004/0175350 A1 | | 9/2004 | Urgell-Beltran et al. |
| 2004/0265443 A1 | | 12/2004 | Beltran et al. |

FOREIGN PATENT DOCUMENTS

| | | |
|---|---|---|
| GB | 1352420 | 5/1974 |
| JP | 10-114618 | 5/1998 |
| WO | 94/19027 | 9/1994 |
| WO | 96/21642 | 7/1996 |
| WO | 01/94292 A1 | 12/2001 |
| WO | 02/087328 A2 | 11/2002 |
| WO | 03/064669 A1 | 8/2003 |
| WO | 03/094638 A1 | 11/2003 |

OTHER PUBLICATIONS

Bastin et al., Organic Process Research and Development, 2000, 4, 427-435.*
International Search Report for PCT/EP2005/053735 dated May 16, 2006, four pages.

* cited by examiner

*Primary Examiner* — Kyle A Purdy
(74) *Attorney, Agent, or Firm* — Rankin, Hill & Clark LLP

(57) ABSTRACT

Preservative systems on the basis of cationic surfactants are known i n the art, a typical example of such cationic surfactants is the ethyl ester of the lauramide of arginine monohydrochloride (LAE) (2). Besides the chloride form the corresponding bromide and sulphate salts are known. It was found that other salts of the cationic surfactants display excellent properties, such as the salts of lactic acid, glutamic acid and acetic acid. It was further found that the combination of the cationic surfactants with at least one salt of an organic or inorganic acid displayed an excellent preservative action. A further preservative system with favourable properties was the combination of the cationic surfactants with at least one ester compound, amide or enzyme inhibitor. Also the combination of the cationic surfactant with a further cationic molecule such as ethyl arginate, glucosamine or chitosan led to an effective preservative system. A further effective preservative system turned out to be the cationic surfactant in encapsulated form.

(2)

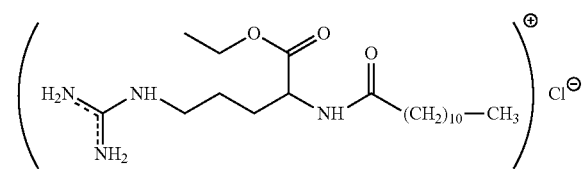

8 Claims, 4 Drawing Sheets

PRESERVATIVE SYSTEMS COMPRISING CATIONIC SURFACTANTS

Figure 1:
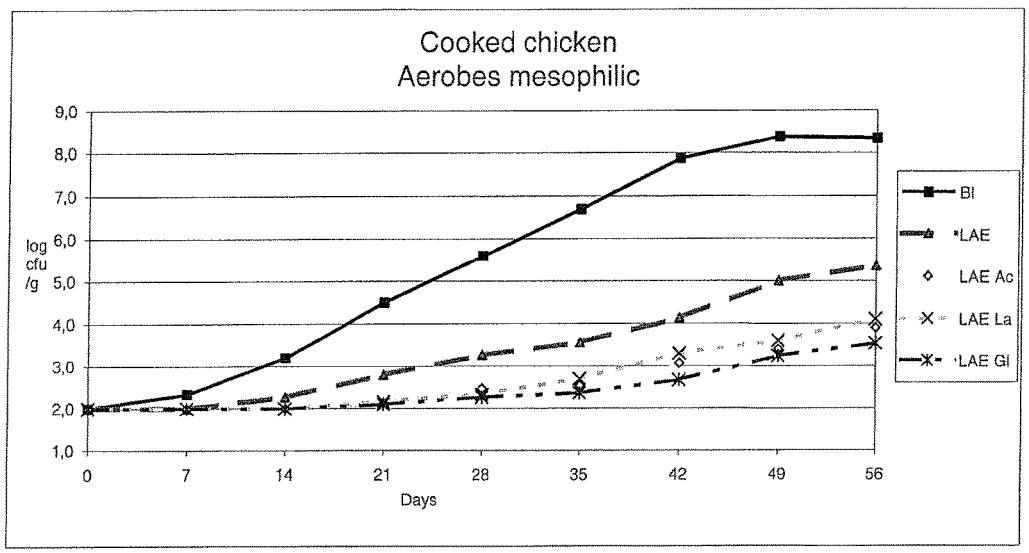

This invention relates to new preservative systems on the basis of cationic surfactants.

In the art it is known to use a preservative system which comprises a cationic surfactant, derived from the condensation of fatty acids and esterified dibasic amino acids, having the formula (1):

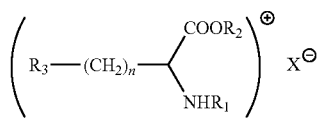

(1)

where:
$X^-$ is $Br^-$, $Cl^-$, or $HSO_4^-$
$R_1$: is a straight alkyl chain of a saturated fatty acid or a hydroxy acid having 8 to 14 carbon atoms linked to the α-amino group via an amide bond,
$R_2$: is a straight or branched alkyl chain from 1 to 18 carbon atoms or an aromatic group and
$R_3$: is:

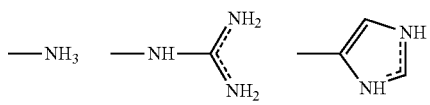

where n is from 0 to 4.

Cationic surfactants are known as preservatives used in the food industry. Due to their composition, food products are susceptible to act as a culture medium for micro-organisms and this constitutes a possible risk to human health. Thus food products require good protection against microbial contamination. During long-time use the class of the cationic surfactants has turned out to be highly effective against microbial proliferation and at the same time safe for intake in humans and mammals in general.

Due to their composition, many cosmetic products are prone to act as a culture medium for micro-organisms, and this can possibly cause changes to the cosmetic preparation and constitute a risk to human health as well. Thus, a cosmetic composition necessarily requires good protection against microbiological contamination. For this reason, a large number of preservatives to inhibit or reduce the microbial population is used.

Most of the preservative systems currently used display incompatibilities with the human skin, such as irritations and allergies and are toxic to human beings as well. On the other hand, it has been demonstrated that cationic surfactants derived from lauric acid and arginine are protective substances against micro-organisms, in particular, the ethyl ester of the lauramide of the arginine monohydrochloride, hereafter referred to as LAE. In practical use LAE turned out to be well tolerated and to display a very low toxicity to human beings. LAE has the chemical structure of formula (2) displayed hereafter. If there will be reference in the present application to the cationic part of the molecule without the negatively charged counter ion this part of the molecule will be identified as the cationic compound $LAE^+$. The whole molecule including the counter ion is characterized dependent on the type of counter ion, LAE is the hydrochloride salt and the corresponding hydrobromic salt would be characterized as LAE bromide or LAE Br.

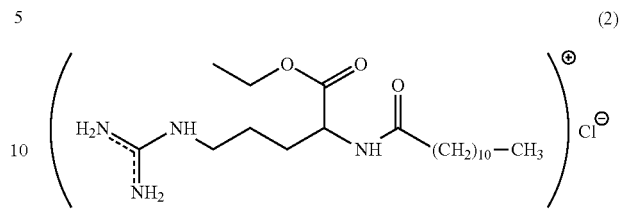

(2)

The compound LAE is remarkable for its activity against different micro-organism, like the bacteria, moulds and yeast which can be present in food products and also in cosmetic formulations and preparations, and its innocuity for humans.

The preparation of the cationic surfactants is described in Spanish patent ES 512643 and international patent applications WO 96/21642, WO 01/94292 and WO 03/064669.

Interactions between the cationic surfactants and other molecules are known. A combination of the cationic surfactants with anionic hydrocolloids is described in WO 03/094638, this combination leads to the generation of solid compounds containing approximately stoichiometric compounds of the cationic surfactant and the anionic hydrocolloid. A further combination of the cationic surfactants is described in WO 02/087328, this combination relating to potassium sorbate, calcium sorbate or sorbic acid, which turned out to be highly effective in food preservation.

These preservative systems described in WO 02/087328 and WO 03/094638 are characterised by their synergetic activity. It has now been found that the antimicrobial activity of the combinations of LAE and the other compounds defined by the above formula (1) with most of the common ionic and non-ionic preservatives used to protect food products and also cosmetic formulations and preparations is higher than the activity displayed by each of the components when used alone at the same dosage. There has been observed synergism when the amounts of the compounds of formula (1) and the other antimicrobial are reduced. Thus, the adverse toxic effects and/or irritation and/or allergy displayed by the combinations of the preservatives have also been reduced.

It has been observed in practical studies that the cationic surfactants are partially hydrolysed with the consequence of the reduction of their biological effects. This phenomenon can be observed in all fresh products which are preserved with the cationic surfactants. It has for instance been observed in the application of LAE in fresh products selected from fish, meat and vegetables. In order to improve the efficacy of the cationic surfactants in such products some tool is required to prolong the biological action of the cationic surfactants.

There is a permanent need in the different technical fields to achieve more effective methods of preservation. In particular there is the broad interest to develop new preservation systems requiring reduced amounts of preservating agents in such areas where direct contact with mammals is involved, such as in the preservation of food preparations and in preservating agents added to cosmetic products, Hence, it is the object of the present invention to provide further preservative systems which are more effective than the preservative systems now known in the art. More specifically, it is the object of the present invention to provide further improved preservative systems on the basis of LAE.

This object is solved by providing the cationic surfactants to be used as preservative agents as a salt of an inorganic or organic acid. As indicated above, the cationic surfactants to be used as preservative agents are known in the art as salts of hydrochloric acid, hydrobromic acid and sulphuric acid, these options of inorganic acids are excluded from the scope of this embodiment of the invention. Otherwise any suitable inorganic or organic acid can be used.

The object is further solved by providing the cationic surfactant in combination with a salt of an organic or inorganic acid or any base. Some salts are already known in combination with cationic surfactants, such as certain salts of sorbic acid, these options are excluded from the scope of the invention.

The object of the invention is also solved by providing a combination of the cationic surfactants according to the invention with another ester compound or with an amide or enzyme inhibitor.

The object of the invention can also be solved by providing the cationic surfactant in combination with a further cationic molecule.

And finally, the object of the invention can be solved by providing the cationic surfactant in a form which makes the molecule less susceptible to hydrolysis through the influence of enzymes or other sources, and also less available for interaction with other substances. According to this aspect of the invention the cationic surfactant is separated from its surroundings through encapsulation in liposomes or micelles, or other similar measures.

Figure 3:
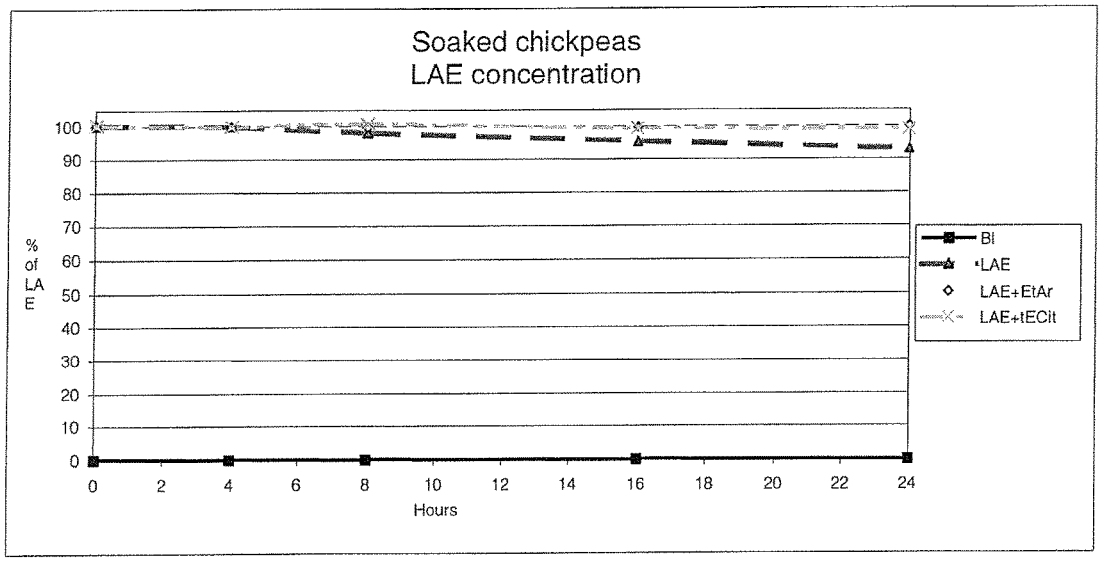
Figure 4:
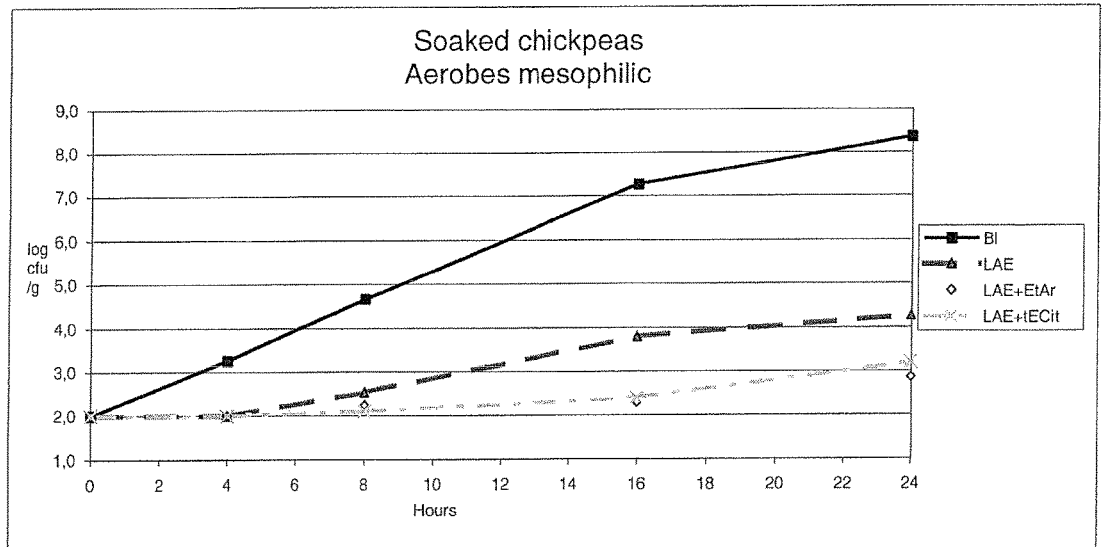
Figure 5:
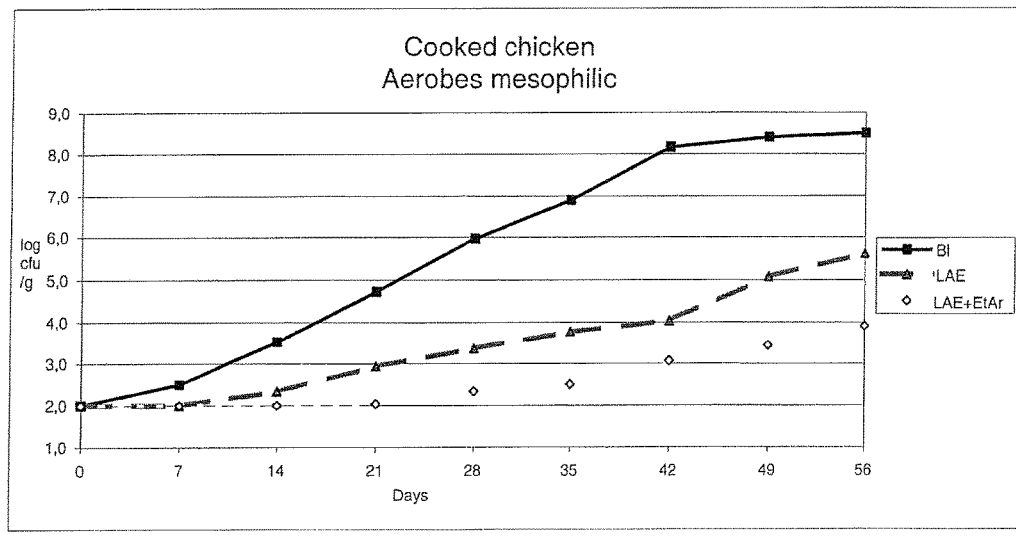
Figure 6:
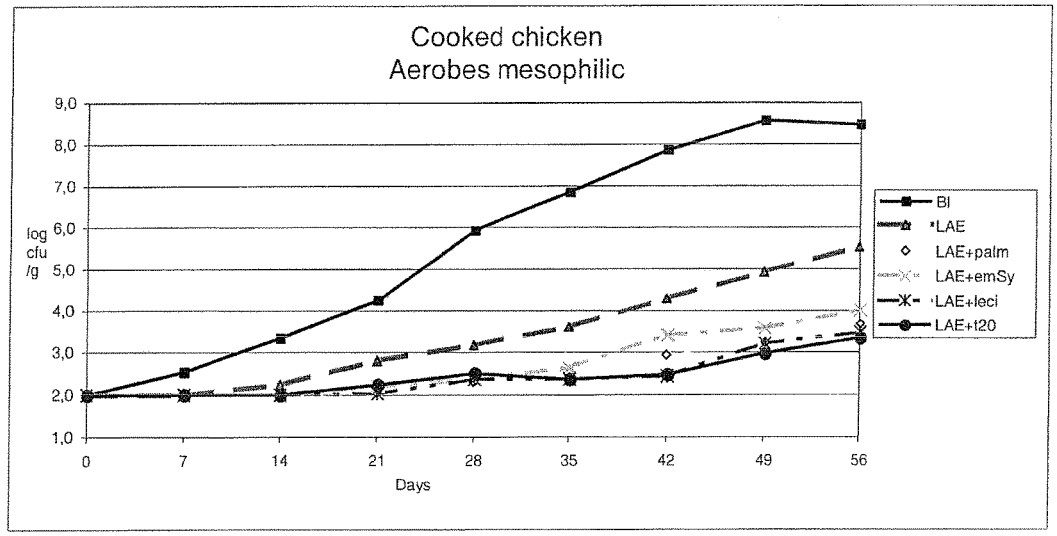

THE APPLICATION CONTAINS THE FOLLOWING DRAWINGS:

FIG. 1. Preservative action of different LAE salts in cooked chicken, mean values of triplicate log cfu/g determination are shown per day and kind of treatment, FIG. 2. Preservative action of combination of LAE with salts in bratwurst sausage, mean values of triplicate log cfu/g determination are shown per day and kind of treatment, FIG. 3. Concentration of LAE after administration of a combination of LAE and esters to soaked chickpeas, the mean values of triplicate concentration determinations of LAE are shown per day and kind of treatment, FIG. 4. Preservative action of combination of LAE with esters in soaked chickpeas, mean values of triplicate log cfu/g determination are shown per day and kind of treatment, FIG. 5. Preservative action of combination of LAE with cationic molecule in cooked chicken, mean values of triplicate log cfu/g determination are shown per day and kind of treatment, FIG. 6. Preservative action of encapsulated LAE in cooked chicken, mean values of triplicate log cfu/g determination are shown per day and kind of treatment.

Figure 7:
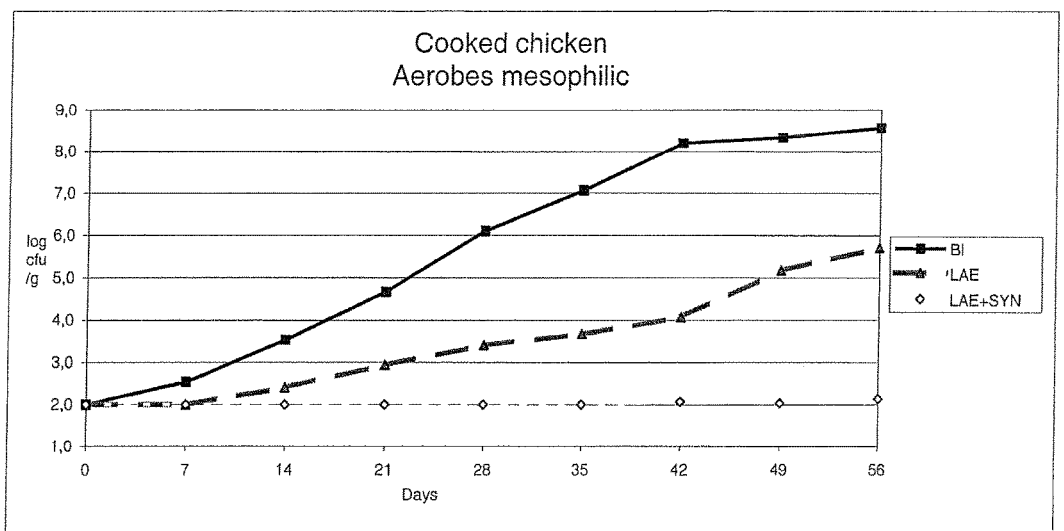

FIG. 7. Preservative action of combination of encapsulated LAE as the acetate salt in combination with other ester compounds and a salt of an organic acid in cooked chicken, mean values of triplicate log cfu/g determination are shown per day and kind of treatment.

I. Salts of Cationic Surfactants

The aspect of providing new, more effective salts of the cationic surfactants is now described.

The present application describes some new product forms of the cationic surfactants of the formula (1), in particular new salts.

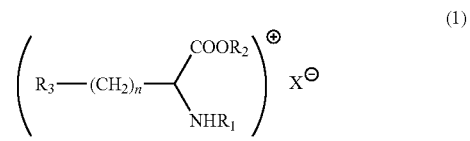

$$\left( R_3-(CH_2)_n-\overset{COOR_2}{\underset{NHR_1}{<}} \right)^{\oplus} X^{\ominus} \quad (1)$$

In the formula (1) the definition of n and the groups $X$, $R_1$, $R_2$ and $R_3$ is as previously described.

These new product forms of the cationic surfactants are also covered by the general term "cationic surfactants", so that where there is a reference in the present application to "cationic surfactants", these new product forms, more in particular these new salts, are included.

The counter ion $X^-$ defined in the above formula (1) is the counter ion which is known in the art. According to the first aspect of the present invention the corresponding cationic surfactants are provided with counter ions which are different from chloride, bromide and sulphate.

The usual organic acids may be used as source for obtaining the further counter ion. Such organic acids are for instance citric acid, lactic acid, acetic acid, fumaric acid, maleic acid, gluconic acid, propionic acid, sorbic add, benzoic acid, carbonic acid, glutamic acid or other amino acids, lauric acid and fatty acids such as oleic acid and linoleic acid.

The usual inorganic acids may be used as source for obtaining the further counter ion. Such usual inorganic acids are for instance phosphoric acid, nitric acid and thiocyanic acid. The mono- and dehydrogenated forms of phosphoric acid qualify as suitable anions.

A further option is an anion on the basis of a phenolic compound. Such phenolic compounds are for instance the butylated hydroxyanisole (BHA) and the related compound butylated hydroxytoluene (BHT), tertiary butyl hydroquinone (TBHQ), and parabens such as methylparaben, ethylparaben, propylparaben and butylparaben.

As the source of the anion in the cationic surfactants it may be more suitable to use a salt of the previously listed inorganic and organic acids. The usual salts of the organic and inorganic acids can be used.

For the selection of the anion it is not of importance that the original compound, in particular the original acid or the original salt, from which the anion is derived, displays a preservative action by itself. The only criterion is that it must be suitable as an anion in combination with the cationic preservative agent. However, in case the original compound displays a preservative action by itself, then its combination as an anion with the cationic preservative agent may display an even more favourable activity profile, in particular a synergistic preservative action may be observed.

For example, suitable salts of cationic surfactants are the citrate, fumarate, malate, gluconate, laurate, lactate, tertiary butyl hydroquinonate, propylparabenate and phosphate salts.

The preparation of the novel salts of the cationic surfactants can be performed using methods which are usual in the art.

A change of the originally present counter ion can be arranged by means of anionic or cationic ion exchange resins including the following steps
1. Equilibrium and arrangement of the ion exchange resin using the desired final counter ion,
2. Interchange procedure by addition of a cationic surfactant of above formula (1) with $X^-$ being any appropriate base, such as $Cl^-$), 3. Completing the interchange process, 4. Optional purification.

Other conventional ways to produce salts of cationic surfactants may be used as well (i.e. metathesis, straight forward acid-base reaction, etc.).

II. Combination of Cationic Surfactants with Salts

The aspect of the cationic surfactant in combination with a salt of an organic or inorganic acid is now described.

Food products as well as cosmetic products comprise molecules bearing a negative charge. Since the cationic surfactants can easily provide the charged ionic parts of its molecule, the cationic part of the molecule may interact with this negative charge and be therefore reduced to achieve any biological effect.

The purpose for adding salts of organic or inorganic acids or any other suitable organic or inorganic bases is that the negative charges off the salts would interact with the cationic surfactant, so that it would create a protection around the molecule of the cationic surfactant avoiding that the cationic surfactant interacts with the anionic elements in the food products or the cosmetic products. This will lead to an improvement of the biological activity of the cationic surfactant.

In general, the action of bacteria in food products and cosmetic products leads to the acidification of these products. When a combination of the cationic surfactant with a salt or suitable bases is used, an effect of stabilization and controlling of the pH value may be achieved. So, the structure and the efficacy of the cationic surfactant may be maintained.

For the wanted action of the combination any salt of organic or inorganic acids can be selected. Suitable organic acids for the preparation of the salt are citric acid, lactic acid, acetic acid, fumaric acid, maleic acid, glucosic acid, propionic acid, sorbic acid, benzoic acid, carbonic acid, glutamic acid or other amino acids, lauric acid and fatty acids such as oleic acid and linoleic acid. Suitable inorganic acids are phosphoric acid, sulphuric acid, nitric acid and hydrochloric acid.

Salts of these acids with any suitable biocompatible cation can be prepared. Suitable salts are for instance sodium citrate, sodium acetate, sodium glutamate, sodium fumarate, sodium malate, sodium gluconate, sodium laurate, sodium lactate and sodium hexametaphosphate.

Another option is an anion on the basis of a phenolic compound. Such phenolic compounds are for instance the butylated hydroxyanisole (BHA) and the related compound butylated hydroxytoluene (BHT), tertiary butyl hydroquinone (TBHQ), and parabens such as methylparaben, ethylparaben, propylparaben and butylparaben. Suitable phenolic compounds are tertiary butyl hydroquinone, propylparaben, and the suitable salts thereof are for instance sodium tertiary butyl hydroquinonate and sodium propylparabenate.

A further option is the combination of any suitable base with the cationic surfactant. Suitable bases are glucosamine and ethanol amine, the suitable salts thereof are for instance the hydrochloride of glusoamine and the hydrochloride of ethanolamine.

Combination with some salts has already been described in the art, these known combinations are excluded from the scope of the present application. Such known combinations are for instance the combination of LAE with calcium sorbate and potassium sorbate.

The combination of the cationic surfactant with the salt of an organic or inorganic acid can be provided as a solid form or as a liquid. When the combination is provided as a solid form it contains at least one cationic surfactant and at least one salt of an organic or inorganic acid. The cationic surfactant can be any of the known cationic surfactants, it is preferred to use LAE. If LAE is used according to the preferred embodiment it may be provided as the chloride, bromide or sulphate salt as the preparations known in the art, or it may be provided as a different salt as described elsewhere in the present application. Different salts of the same cationic surfactant may be present at the same time. Different cationic surfactants may be present at the same time, which different cationic surfactants may be provided as either the same or different salt.

When the combination of the cationic surfactant with the salt of the organic or inorganic acid is provided as a liquid, any suitable solvent may be used. By dissolving or dispersing the cationic surfactant and the salt of the organic or inorganic acid into the solvent, the object composition can be efficiently produced. Examples of the suitable solvents include monohydric alcohols such as n-butyl alcohol, isobutyl alcohol, sec-butyl alcohol, t-butyl alcohol, n-amyl alcohol, isoamyl alcohol, sec-amyl alcohol, n-hexyl alcohol, methylamyl alcohol, ethylbutyl alcohol, heptyl alcohol, n-octyl alcohol, sec-octyl alcohol, 2-ethylhexyl alcohol, isooctyl alcohol, n-nonyl alcohol, 2,6-dimethyl-4-heptanol, n-decyl alcohol and cyclohexanol; glycols and polyhydric alcohols such as ethylene glycol, diethylene glycol, triethylene glycol, tetraethylene glycol, propylene glycol, dipropylene glycol, 1,4-butylene glycol, 2,3-butylene glycol, hexylene glycol, octylene glycol and glycerol; cellosolves such as ethylene glycol monomethyl ether, ethylene glycol ethyl ether, ethylene glycol diethyl ether, ethylene glycol butyl ether, ethylene glycol dibutyl ether, ethylene glycol phenyl ether, ethylene glycol benzyl ether, ethylene glycol ethyl hexyl ether, diethylene glycol ethyl ether, diethylene glycol diethyl ether, diethylene glycol butyl ether, diethylene glycol dibutyl ether, propylene glycol methyl ether, propylene glycol ethyl ether, propylene glycol butyl ether, dipropylene glycol methyl ether, dipropylene glycol ethyl ether, tripropylene glycol methyl ether, tetraethylene glycol dimethyl ether and tetraethylene glycol dibutyl ether; crown ethers such as benzo-15-crown-5, benzo-12-crown-4, benzo-18-crown-6 and dibenzo-18-crown-6; ketones such as ethyl butyl ketone, dipropyl ketone, methyl amyl ketone, methyl hexyl ketone and diisobutyl ketone; and fatty acids such as fatty acids having 3 to 30 carbon atoms described above.

The concentration of the salt of an organic or inorganic acid dissolved or dispersed into the above solvent is not particularly limited and can be suitably selected in accordance with the circumstances.

III. Combination of Cationic Surfactants with Ester Compounds, Amides or Enzyme Inhibitors The further aspect of providing the cationic surfactant in combination with another ester compound or amide is now described.

A large variety of ester compounds and amides may be used. Suitable ester compounds for this aspect of the invention are triethyl citrate, triacetine, diacetine, esters of glycerol, esters of amino acids and esters of fatty acids. If appropriate, combinations of these esters may be used. A suitable amide is the acetamide of arginine.

The cationic surfactant may be present in the combination with the further ester compound as a conventional bromide, chloride or sulphate salt. It is more suitable to use the cationic surfactant as the salt of acetic acid, lactic acid or glutamic acid.

There is no scientific proof for the reason of the efficacy of the combination of the above cationic surfactants with other ester compounds or amides, but it is assumed that the presence of a further esterified compound or amide may lead to a delay in the enzymatic breakdown of the molecules of the cationic surfactant due to a competition-like phenomenon. For the antimicrobial effect of the above cationic surfactants the molecule has to be intact. Hydrolysis of the ester or amide bond reduces the antimicrobial effect of the compounds.

The more labile binding present in the cationic surfactants is the ester function yielding the correspondent acid. The amide bound is far more stable but may also be affected by some type of enzymes.

Since it is the intention of the combination of the cationic surfactants with the further ester compound to reduce the breakdown through enzymatic influence, it is obvious that the same final effect as achieved through the combination with a further ester compound can be achieved through the combination with a compound which inhibits the enzymatic hydrolysing activity directly. Such an enzyme inhibitor is for instance the product genistein.

The cationic surfactants have a structure which is easily recognised by the natural metabolising capacity of living creatures. This is one of the main reasons to explain its low toxicity. One of the drawbacks of this characteristic is that the cationic surfactants may be partially hydrolysed by natural enzymes present in many food products. Food products that have raw ingredients (vegetables, meat, fish, etc.) and any food products in the preparation of which a raw product is added (even if finally these food products are cooked) are potentially able to reduce the effective concentration of the cationic surfactants.

It has been found by the inventors that the addition of enzyme inhibitors improves the efficacy of the cationic surfactants in these types of products. Moreover, the addition of simple esters or amides, which are not known as specific enzymatic inhibitors, delays the hydrolysis of the cationic surfactants and improves their efficacy. Even if degradation is not significant (5-10% of the initial amount of the cationic surfactants) the efficacy is substantially improved, probably, because homogeneity/efficiency is better.

Many cosmetic products contain natural additives that may have still some remnant enzymatic activity. Apart from that, cosmetic products, by definition, are applied onto the skin, inside the mouth, etc. In all these applications cosmetic products will arrive to be in contact with active enzymes.

As in food products it has been found out that the addition of enzymatic inhibitors improves the efficacy of in cosmetic products. Moreover, the addition of simple esters or amides, which are not known as specific enzymatic inhibitors, delay hydrolysis of the cationic surfactants and improves their efficacy. Even if degradation is not significant (5-10% of the initial amount of the cationic surfactants) the efficacy is substantially improved, probably, because the efficiency is better.

Suitable enzymatic delayers and inhibitors are for instance esters, amides and enzyme inhibitors such as listed hereafter.

Esters:
 1. Any alcohol ester of amino acids, i.e. ethyl arginate,
 2. Fatty acids esters of glycerol, mono, di- and triacylglycerides,
 3. Triacetin, diacetin,
 4. Fatty acid esters of ascorbic acid,
 5. Acetic, lactic, citric, tartaric esters of mono and diglycerides,
 6. Sucroesters of fatty acid,
 7. Sucroglycerides,
 8. Any other suitable ester molecules.

Amides:
 1. Natural peptides, dipeptides, proteins, etc.,
 2. Any suitable amide molecules, e.g. acetamide of arginine.

Enzyme Inhibitors:
 1. Genistein,
 2. Sugars and peptides of lupin,
 3. Any other suitable enzymatic inhibitors.

Preferred esters in connection with this aspect of the invention are methyl arginate, ethyl arginate and propyl arginate.

The combination of the cationic surfactant with the ester, the amide or the enzyme inhibitor may be provided in solid or in liquid form. If the combination of the cationic surfactant with an ester, an amide or an enzyme inhibitor is provided in a liquid form, various solvents can be used. Examples of the solvent include monohydric alcohols such as n-butyl alcohol, isobutyl alcohol, sec-butyl alcohol, t-butyl alcohol, n-amyl alcohol, isoamyl alcohol, sec-amyl alcohol, n-hexyl alcohol, methylamyl alcohol, ethylbutyl alcohol, heptyl alcohol, n-octyl alcohol, sec-octyl alcohol, 2-ethylhexyl alcohol, isooctyl alcohol, n-nonyl alcohol, 2,6-dimethyl-4-heptanol, n-decyl alcohol and cyclohexanol; glycols and polyhydric alcohols such as ethylene glycol, diethylene glycol, triethylene glycol, tetraethylene glycol, propylene glycol, dipropylene glycol, 1,4-butylene glycol, 2,3-butylene glycol, hexylene glycol, octylene glycol and glycerol; cellosolves such as ethylene glycol monomethyl ether, ethylene glycol ethyl ether, ethylene glycol diethyl ether, ethylene glycol butyl ether, ethylene glycol dibutyl ether, ethylene glycol phenyl ether, ethylene glycol benzyl ether, ethylene glycol ethyl hexyl ether, diethylene glycol ethyl ether, diethylene glycol diethyl ether, diethylene glycol butyl ether, diethylene glycol dibutyl ether, propylene glycol methyl ether, propylene glycol ethyl ether, propylene glycol butyl ether, dipropylene glycol methyl ether, dipropylene glycol ethyl ether, tripropylene glycol methyl ether, tetraethylene glycol dimethyl ether and tetraethylene glycol dibutyl ether; crown ethers such as benzo-15-crown-5, benzo-12-crown-4, benzo-18-crown-6 and dibenzo-18-crown-6; ketones such as ethyl butyl ketone, dipropyl ketone, methyl amyl ketone, methyl hexyl ketone and diisobutyl ketone; and fatty acids such as fatty acids having 3 to 30 carbon atoms described above.

IV. Combination of Cationic Surfactants with Other Cationic Compounds

The further aspect of providing the cationic surfactant in combination with another cationic compound is now described.

Due to their high cationic surfactant characteristics the cationic surfactants have the tendency to attach to anionic sites of complex matrices to which they are applied. Such complex matrices cover food products and cosmetic formulations. These anionic sites in the complex matrices may comprise be proteins, glycoproteins, surfactants, silica, etc.

If the cationic surfactants are mixed with other cationic molecules their activity is surprisingly improved. This is because the cationic surfactants are more free to attach to microorganisms than to other anionic sites which have already blocked by the added cationic molecules. In other words the availability of anionic sites in the material which is to be treated through the application of the cationic surfactants is reduced.

The other cationic molecule which is mixed with the cationic surfactants does not have to display necessarily any preservative effect of its own. Of course, if the other cationic molecule has some known preservation activity (even if it is slight) then synergy may be observed and the combination may in that case be surprisingly effective.

The other cationic molecules can be selected from the following general groups of compounds:
1. glucosamine and other monosacharide-amines,
2. chitosan, oligomers of chitosan and other polyamines like polylysine, etc.,
3. cationic polysacharides (i.e. cationic starch),
4. cationic aminoacids and peptides, e.g. glutamic acid,
5. esters of aminoacids,
6. lipoplexes and
7. any other suitable cationic molecule.

Suitable examples of the above cationic agents are the esters of amino acids, more in particular ethyl arginate.

The combination of the cationic surfactant with the other cationic compound may be provided in solid or in liquid form. If the combination of the cationic surfactant with an ester, an amide or an enzyme inhibitor is provided in a liquid form, various solvents can be used. Examples of the solvent include monohydric alcohols such as n-butyl alcohol, isobutyl alcohol, sec-butyl alcohol, t-butyl alcohol, n-amyl alcohol, isoamyl alcohol, sec-amyl alcohol, n-hexyl alcohol, methylamyl alcohol, ethylbutyl alcohol, heptyl alcohol, n-octyl alcohol, sec-octyl alcohol, 2-ethylhexyl alcohol, isooctyl alcohol, n-nonyl alcohol, 2,6-dimethyl-4-heptanol, n-decyl alcohol and cyclohexanol; glycols and polyhydric alcohols such as ethylene glycol, diethylene glycol, triethylene glycol, tetraethylene glycol, propylene glycol, dipropylene glycol, 1,4-butylene glycol, 2,3-butylene glycol, hexylene glycol, octylene glycol and glycerol; cellosolves such as ethylene glycol monomethyl ether, ethylene glycol ethyl ether, ethylene glycol diethyl ether, ethylene glycol butyl ether, ethylene glycol dibutyl ether, ethylene glycol phenyl ether, ethylene glycol benzyl ether, ethylene glycol ethyl hexyl ether, diethylene glycol ethyl ether, diethylene glycol diethyl ether, diethylene glycol butyl ether, diethylene glycol dibutyl ether, propylene glycol methyl ether, propylene glycol ethyl ether, propylene glycol butyl ether, dipropylene glycol methyl ether, dipropylene glycol ethyl ether, tripropylene glycol methyl ether, tetraethylene glycol dimethyl ether and tetraethylene glycol dibutyl ether; crown ethers such as benzo-15-crown-5, benzo-12-crown-4, benzo-18-crown-6 and dibenzo-18-crown-6; ketones such as ethyl butyl ketone, dipropyl ketone, methyl amyl ketone, methyl hexyl ketone and diisobutyl ketone; and fatty acids such as fatty acids having 3 to 30 carbon atoms described above.

V. Cationic Surfactants in Encapsulated Form

The further aspect of providing the cationic surfactant in encapsulated or otherwise physically protected form is now described Processed foods and cosmetic products comprise some molecules or additives that have a negative charge. Since the cationic surfactants are cationic molecules, they may interact with this negative charge and the activity of the cationic surfactants as preservative would accordingly be reduced.

Apart from that, these cationic preservatives possess a structure which is easily recognised by natural metabolism of living creatures. This is one of the main reasons to explain its low toxicity. One of the drawbacks of this characteristic is that the cationic surfactants may be partially hydrolysed by natural enzymes present in many food and cosmetic products and/or in many food or cosmetic applications.

Encapsulation/covering techniques (physical, chemical, due to surfactant characteristics of the cationic surfactants) are known ways to protect additives and ingredients from aggressive storage conditions or in order to modify release speed of these products. Surfactant characteristics of the cationic surfactants imply a great potential variety of auto-aggregation structures (micelles, crystal liquids, etc.).

In theory these techniques would not be helpful in order to avoid contact of the cationic surfactants with anionic sites and or enzymes, because once the cationic surfactant was released it would immediately interact either with anionic sites or with enzymes and therefore its activity would be decreased as if it was not covered.

Surprisingly, covering of the cationic surfactants by physicochemical means increases their efficiency. Taking advantage of different auto-aggregation structures is also increasing the efficiency of the cationic surfactants. It has been observed that different encapsulation techniques lead to an improved stability under different circumstances of temperature, pH, humidity and others. It also improves the stability of the cationic surfactants against the influence of enzymatic breakdown.

Explanations for this unexpected behaviour may be based on the fact that the cationic surfactants interact preferably with micro-organisms than with anionic sites and or enzymes and once it has made contact to the micro organisms this contact is permanent and irreversible. Therefore all these encapsulation techniques lead eventually to an increase the activity of the cationic surfactants.

Encapsulation techniques may be based on physical methods (spray chilling, spray drying, rotary disk atomisation, fluid bed coating, stationary nozzle co-extrusion, centrifugal head co-extrusion, submerged nozzle co-extrusion, pan coating, etc.).

Or, on chemical methods (phase separation, solvent evaporation, solvent extraction, interfacial polymerisation, simple and complex coacervation, in-situ polymerisation, liposome technology, nano-encapsulation, etc.).

Due to surfactant characteristics of the cationic surfactants other potential ways to encapsulate/cover the cationic surfactants or physically/chemically change the way to add the cationic surfactants may exist. For example, mixed micelles, emulsions oil in water, emulsions water in oil, micro emulsions (o/w, w/o or bicontinuous), multiple layered emulsion, solubilization of the cationic surfactants in different solvents or with different salts or products dissolved in order to change auto-aggregation of the cationic surfactants (micelles (size and quantity), crystal liquid, etc.), etc.

The following coating agents may be used:
1. vegetable, animal, or mineral oils, e.g. palm oil (35-80° C. melting point);
2. vegetable, animal or mineral fats;
3. vegetable or animal biopolymers;
4. surfactants (non-ionic, anionic, cationic);
5. lecithin;
6. cyclodextrins and
7. any other suitable product which may cover the cationic surfactants.

VI. Combination of Different Efficacy Improvements

In the previous sections I to V different preservative systems have been described, each with the aim of improving the preservative systems which are known in the art. Different solutions for the improvement of the biological activity of cationic surfactants such as LAE have been found. Each of these solutions is capable of improving the effect achieved by the addition of LAE alone.

It is possible to combine the different solutions described in the previous sections. In the section I the difference of the biological activity of different salts of LAE have been described. Salts of sulphuric acid, hydrochloric acid and hydrobromic acid were known in the art and the improvement through the replacement of the counter ion with other counter ions such as acetate, glutamate and lactate was surprisingly detected. A further option for improvement is the combination of cationic surfactants such as LAE with a salt of an organic or inorganic acid. It was found that the combination of LAE with a salt of an organic acid such as for instance sodium citrate led to an improvement of the biological efficacy. This proof could be provided for the usual version of LAE which is the chloride form. It is an obvious further option according to the invention to combine the different solutions of the invention. So, it is a further embodiment of the present invention to combine the different salts of LAE, such as for instance the acetate salt, the glutamate salt and the lactate salt with a salt of inorganic or organic acid. In the similar manner the other embodiments according to the invention may be combined to obtain further improved embodiments.

EXAMPLES

The invention is now explained in more detail through the following examples.

For the determination of the effects achieved by the preservative systems according to the invention the following experimental methods are used:

(1) Determination of Preservative Action in Cosmetic Products.

The method is based on the *Antimicrobial Effectiveness Testing* USP 24$^{th}$ Edition, 1999 (pp. 1809-1811). Its purpose is the demonstration that the antimicrobial activity of the preservative systems according to the invention is enough to avoid unwanted microbial growth which could have a negative impact on the storage and use of the preparation, and to prevent the adverse effects of the contamination (Real Farmacopea Española, 1$^{st}$ Edición, 1997).

This assay consists of the contamination of the protecting formulations with an inoculum mixture of $10^8$ cfu/ml concentration, for each of the micro-organisms, and the determination of the number of viable cells in time. This inoculum mixture is composed of the following microorganisms:

| | |
|---|---|
| *Pseudomonas aeruginosa* | ATCC 9027 |
| *Staphylococcus aureus* | ATCC 6538 |
| *Candida albicans* | ATCC 10231 |
| *Aspergillus niger* | ATCC 16404 |
| *Escherichia coil* | ATCC 8739 |

The cosmetic composition to be analysed is divided into sterile containers with 50 g of product for each flask. Each container is inoculated with 0.5 ml of inoculum ($10^8$ cfu/ml). The target concentration is $10^6$ cfu/ml, approximately. All the containers are kept at a temperature between 20-25° C. and are protected from light.

The level of the microbial contamination is checked at 0 hours, 7 days, 14 days and 28 days. The number of colonies is evaluated by dilution in buffer peptone with the appropriate neutraliser agent of the preservative. The culture media used for counting the microorganisms are: Soya triptone (35-37° C., 48 hours) for the determination of bacteria; Sabouraud agar with chloramphenicol for fungi and yeast (25° C., 3-5 days).

According to *Antimicrobial Effectiveness Testing* USP 24th Edition, 1999 (pp. 1809-1811), an antimicrobial preservative is considered to be effective in topically used products made with aqueous bases or vehicles, non-sterile nasal products and emulsions, including those applied to mucous membranes, if:

not less than 2.0 logarithm reduction from the initial calculated bacteria's count is reached at 14 days and no increase from the 14 days' count at 28 days is detected; and no increase from the initial calculated count of yeast and moulds is observed.

(2) Determination of Preservative Action in Chicken Breast.

Process of Preparation

1. Fresh chicken breast was diced to pieces
2. Brine (8.70% sodium chloride and 4.35% tripolyphosphate in water) was added to the fresh chicken in an amount of 11.5 g brine per 88.5 g meat in the control preparation and 11.5 g brine and 88.4 g meat in the preparations treated with preservative.
3. Brine and meat were mixed during 15 minutes, in the preparations treated with preservative the preservative was added after 14 minutes in an amount of 0.2 g/kg.
4. Vacuum refrigerate tumbling was made during 30 minutes.
5. Samples were vacuum-packed in sterile bags and they were cooked at 85° C. for 30 minutes.
6. The cooked chicken was refrigerated at 4° C.
7. The cooked chicken was diced in irregular shapes.
8. Then, the nuggets were stored at 10° C. in sterile vacuum-packed bags.

Analysis

Samples were analysed in triplicate (aerobic total count) after storage for 7, 14, 21, 28, 35, 42, 49 and 56 days. Aerobic total count was analysed by stomaching 25 g of each sample in 225 g of buffered peptone water. Dilutions were made in buffered peptone water. Tryptone Soya Agar was harvested with each dilution and incubated at 35° C. for 48 hours.

The mean value in log cfu/g of three samples per treatment and day of analysis was calculated.

(3) Determination of Preservative Action in Bratwurst Sausage.

Bratwurst Sausage

Process of Preparation

The ingredients for all samples were : minced pork back, underbelly, spices, salt and additives (milk protein, diphosphate, antioxidant (E-300) and flavour enhance (E-621)).

1. On the cutter the minced pork back meat was ground and the ingredients were added in this order: the additives (except the preservative system), the underbelly, the spices and the preservative system (such as the cationic surfactant alone or in combination with other products). Ice was also added for controlling the temperature (maximum 5° C.) of the meat. The mixing time was 12 minutes.
2. The mass was vacuum mixed (92%) for 1 minute.
3. The mixture was stuffed into natural casings. The casings were previously soaked in a salted water solution for 30 minutes.
4. The bratwurst sausages were put in a cooking trolley. Cooking took place in a oven at 80° C. for 1 hour.
5. After cooking, the bratwurst sausages were sprayed with cool water for 5 minutes and put in a cold-storage room (0-5° C., 24 hours).
6. The next day, bratwurst sausages were packed (each packed contained five sausages) and pasteurised at 80° C. for 30 minutes and then. After, they were soaked in cool water for 30 minutes.
7. Finally, the bratwurst sausages were labelled and stored at 5° C. for 90 days.

Analysis

Samples were analysed (aerobic total count) for up to 90 days. Aerobic total count was analysed by stomaching 25 g of sausage in 225 g of buffered peptone water. Dilutions were made in buffered peptone water. Tryptone Soya Agar was harvested with each dilution and incubated at 35° C. for 48 hours.

Average values in log cfu/g of three samples per treatment and day of analysis were calculated.

(4) Determination of Preservative Action in Soaked Chickpeas.

Soaked Chickpeas

Chickpeas are the principal ingredients in a lot of ready-to-eat meals. Before cooking them, chickpeas have to be soaked in water at room temperature for 24 hours. During this period, fermentation processes may occur and therefore, chickpeas would not be suitable for eating. The soaking process cannot be made at refrigeration temperatures, because the structure of the chickpeas could be damaged.

Process of Preparation

1. Chickpeas were soaked in water for 24 hours at 30° C. and 50% HR (in treated samples preservative was added at this point); and
2. after 24 hours the chickpeas were strained.

Analysis

Samples were analysed (aerobic total count and concentration of the cationic surfactant) by triplicate for 24 hours.

Aerobic total count was analysed by stomaching 25 g of chickpeas in 225 g of buffered peptone water. Dilutions were made in buffered peptone water. Tryptone Soya Agar was harvested with each dilution and incubated at 35° C. for 48 hours.

Average values in log cfu/g of three samples per treatment and day of analysis were calculated.

LAE was analysed by HPLC using an internally validated method.

In the following specific examples the products according to the invention and the antimicrobial effects displayed by them are described in more detail.

Example 1 (Reference).

Preparation of LAE Chloride

Preparation of LAE chloride (LAE) was performed in the manner as described in the international patent applications WO 96/21642 and WO 01/94292.

Example 2

Preparation of LAE Acetate

The resin Amberlite IRA402 (as the chloride form) was washed with water. A solution of sodium acetate (Fluka) was introduced and thereafter the resin was washed with water again. A solution of LAE was introduced in the resin column and fractions were collected. The collected fractions were lyophilzed. LAE acetate is obtained as a solid white powder.

Example 3

Preparation of LAE Lactate.

The resin Amberlite IRA402 (as the chloride form) was washed with water. A solution of sodium lactate (Fluka) was introduced and thereafter the resin was washed with water again. A solution of LAE was introduced in the resin column and fractions were collected. The collected fractions were lyophilzed. LAE lactate is obtained as a solid white powder.

Example 4

Preparation of LAE Glutamate.

The resin Amberlite IRA402 (as the chloride form) was washed with water. A solution of sodium glutamate (Fluka) was introduced and thereafter the resin was washed with water again. A solution of LAE was introduced in the resin column and fractions were collected. The collected fractions were lyophilzed. LAE lactate is obtained as a solid white powder.

Example 5

LAE Encapsulated with Palm Oil (LAE+Palm)
20 g hot molten palm oil was sprayed at 60° C. over 80 g LAE in a High Shear Mixer machine. The final product was cooled to room temperature.
Palm oil was obtained at the company Vandermoortele.

Example 6

LAE Emulgated with Soybean Oil (LAE+emSy)
20 g LAE was dissolved in 60 g hot water, stirring with Ultra Turrax®, was performed, 20 g soybean oil was added slowly under stirring and the final product was cooled very fast.
Soybean oil was obtained at the company Mateo.

Example 7

LAE in Lecithin (LAE+Leci)
10 g LAE and 10 g lecithin were dissolved in THF at 30° C., evaporating THF at 70° C., dispersing the mix in water and extrusion through a 200 nm membrane 5 times.
Lecithin was obtained at Aldrich.

Example 8

LAE with Tween 20 (LAE+T20)
20 g LAE Cl and 20 g Tween 20 were dissolved in 60 g water.
Tween was obtained at Panreac.

Example 9

Salts of Cationic Surfactants
Application in Food Products

As a test method the determination of the preservative action in chicken breast was chosen.

Treatments

The preparation of the products used in this example has been described in examples 1 to 4.

| | |
|---|---|
| 1. Control (no treatment added): | BI |
| 2. LAE 0.2 g/kg: | LAE |
| 3. LAE acetate 0.2 g/kg: | LAE Ac |
| 4. LAE lactate 0.2 g/kg: | LAE La |
| 5. LAE glutamate 0.2 g/kg: | LAE Gl |

All concentrations in the above treatments relate to the amount of the preservative cationic surfactant per kg of final product.

Results

The experimental data are provided in table 1. A graphical representation is displayed in FIG. 1.

Samples of cooked chicken treated with LAE have counts below 4.0 log cfu/g for 5 weeks.

Control samples at the same time have 6.7 log cfu/g which can be considered as being already spoiled.

In contrast, samples of chicken treated with LAE$^+$ combined with acetate, lactate or glutamate have counts below 4.0 log cfu/g even at 8 weeks (3 weeks later than with LAE).

At 8 weeks samples of chicken treated with LAE combined with acetate, lactate or glutamate are 1.5 log cfu/g below samples of chicken treated with LAE.

All treated samples have a nice and correct appearance at the end of the experiment.

Control samples at 8 weeks have arrived to 8.3 log cfu/g, they smell very badly and the presence of viscous liquid is detected.

TABLE 1

Results of aerobic total count

|  | BI | LAE | LAE Ac | LAE La | LAE Gl | Days |
|---|---|---|---|---|---|---|
| 1 | 2.0 | 2.0 | 2.0 | 2.0 | 2.0 | 0 |
| 2 | 2.0 | 2.0 | 2.0 | 2.0 | 2.0 |  |
| 3 | 2.0 | 2.0 | 2.0 | 2.0 | 2.0 |  |
| mean | 2.0 | 2.0 | 2.0 | 2.0 | 2.0 |  |
| 1 | 2.0 | 2.0 | 2.0 | 2.0 | 2.0 | 7 |
| 2 | 2.5 | 2.0 | 2.0 | 2.0 | 2.0 |  |
| 3 | 2.5 | 2.0 | 2.0 | 2.0 | 2.0 |  |
| mean | 2.3 | 2.0 | 2.0 | 2.0 | 2.0 |  |
| 1 | 3.4 | 2.0 | 2.0 | 2.0 | 2.0 | 14 |
| 2 | 3.0 | 2.5 | 2.0 | 2.0 | 2.0 |  |
| 3 | 3.2 | 2.3 | 2.0 | 2.0 | 2.0 |  |
| mean | 3.2 | 2.3 | 2.0 | 2.0 | 2.0 |  |
| 1 | 4.5 | 3.0 | 2.1 | 2.1 | 2.1 | 21 |
| 2 | 4.6 | 2.8 | 2.3 | 2.4 | 2.2 |  |
| 3 | 4.4 | 2.6 | 2.0 | 2.0 | 2.0 |  |
| mean | 4.5 | 2.8 | 2.1 | 2.2 | 2.1 |  |
| 1 | 5.7 | 3.1 | 3.0 | 2.6 | 2.5 | 28 |
| 2 | 5.5 | 3.2 | 2.1 | 2.1 | 2.1 |  |
| 3 | 5.6 | 3.5 | 2.3 | 2.3 | 2.2 |  |
| mean | 5.6 | 3.3 | 2.5 | 2.3 | 2.3 |  |
| 1 | 6.7 | 3.6 | 2.3 | 2.8 | 2.3 | 35 |
| 2 | 6.9 | 3.8 | 2.8 | 2.8 | 2.5 |  |
| 3 | 6.5 | 3.3 | 2.5 | 2.5 | 2.3 |  |
| mean | 6.7 | 3.6 | 2.5 | 2.7 | 2.4 |  |
| 1 | 7.9 | 4.0 | 3.1 | 3.1 | 2.6 | 42 |
| 2 | 7.5 | 4.3 | 2.8 | 3.5 | 2.8 |  |
| 3 | 8.2 | 4.1 | 3.3 | 3.3 | 2.6 |  |
| mean | 7.9 | 4.1 | 3.1 | 3.3 | 2.7 |  |
| 1 | 8.5 | 5.1 | 3.3 | 3.3 | 3.2 | 49 |
| 2 | 8.5 | 4.7 | 3.0 | 3.6 | 3.0 |  |
| 3 | 8.1 | 5.2 | 3.9 | 3.9 | 3.5 |  |
| mean | 8.4 | 5.0 | 3.4 | 3.6 | 3.2 |  |
| 1 | 8.3 | 5.3 | 3.8 | 4.2 | 3.5 | 56 |
| 2 | 8.1 | 5.2 | 4.0 | 4.0 | 3.8 |  |
| 3 | 8.6 | 5.5 | 3.9 | 3.9 | 3.3 |  |
| mean | 8.3 | 5.4 | 3.9 | 4.1 | 3.5 |  |

All results expressed in log cfu/g

Example 10

Salts of Cationic Surfactants
Application in Cosmetic Products

As a test method the above method for the determination of preservative action in cosmetic products was chosen.

Oil in Water Emulsion

The composition of the cosmetic formulation in oil-in-water emulsion, with non-ionic surfactant, is (in g):

| Polysorbate 60 | 3.00 |
|---|---|
| Sorbitan stearate | 2.00 |
| Cetyl alcohol | 1.00 |
| Paraffinum | 3.00 |
| Isopropyl myristate | 3.00 |
| Caprylic-caproic triglycerides | 3.00 |
| Dimethicone | 0.50 |
| Propylene glycol | 3.00 |
| Cellulose gum | 0.25 |
| Carbomer 940 | 0.10 |
| Triethanolamine | 0.10 |
| Aqua | 100 c.s.p. |

The used products were obtained at the following sources: Polysorbate 60: Uniqema; sorbitan stearate: Uniqema; cetyl alcohol: Degussa; paraffinum: Impex; isopropyl myristate: Degussa; caprylic-caproic triglycerides: Degussa; dimethicone: Degussa; propylene glycol: Quimidroga; cellulose gum: Hercules; carbomer 940: Degussa and triethanolamine: Quimidroga.

The preparation of the oil in water emulsion was as follows: the oil ingredients (polysorbate 60, sorbitan stearate, cetyl alcohol, paraffinum, isopropyl myristate, caprylic-caproic triglycerides, dimethicone) were mixed together and heated at 75° C. The water phase (consisting of propylene glycol, cellulose gum, carbomer 940 and aqua) was also heated to 75° C.

The oil phase was added to the water phase under stirring of approximately 5000 rpm by Ultraturrax. The emulsion was completed in 2 minutes. The emulsion was cooled fast to room temperature while stirring at a low speed of 20 rpm. Triethanolamine was added to adjust the pH to 6-7.

This formulation is completed with the different preservative systems and their capacity of preservation is evaluated against the formulation without LAE (control).

| 1. Control (no treatment added): | BI |
|---|---|
| 2. LAE 0.2 g/kg: | LAE |
| 3. LAE acetate 0.2 g/kg: | LAE Ac |
| 4. LAE lactate 0.2 g/kg: | LAE La |
| 5. LAE glutamate 0.2 g/kg: | LAE Gl |

The indicated concentration is in g per kg of the oil in water emulsion.

The results are shown in the next table 2.

TABLE 2

|  | Microorganism | BI | LAE | LAE Ac | LAE La | LAE Gl |
|---|---|---|---|---|---|---|
| 0 days | Aerobes | 6.5 | 6.2 | 6.0 | 6.1 | 6.1 |
|  | Moulds | 4.4 | 4.3 | 4.1 | 4.2 | 4.1 |
|  | Yeast | 5.5 | 5.6 | 5.3 | 5.4 | 5.6 |
| 7 days | Aerobes | 6.9 | 3.5 | 2.5 | 2.2 | 2.3 |
|  | Moulds | 3.1 | <2.0 | <2.0 | <2.0 | <2.0 |
|  | Yeast | 4.9 | 3.4 | 2.1 | 2.2 | 2.4 |
| 14 days | Aerobes | 7.3 | 3.0 | <2.0 | <2.0 | <2.0 |
|  | Moulds | 3.4 | <2.0 | <2.0 | <2.0 | <2.0 |
|  | Yeast | 4.7 | 2.6 | <2.0 | <2.0 | <2.0 |

The results are provided in log cfu/g.

At 28 days no increase is detected compared with the count at 14 days.

Therefore, it is clear that oil in water emulsions treated with LAE and LAE$^+$X$^-$ where X$^-$ is acetate, lactate and or glutamate are effectively preserved.

Changing the counterion CF$^-$ for other anions (such as acetate, lactate or glutamate) increases log reductions of inoculated microorganisms by more than 1 log cfu/ml.

Preservation with LAE$^+$X$^-$ where X$^-$ is acetate, lactate and or glutamate is improved compared to LAE.

Example 11

Combination with Salts of Organic/Inorganic Acids
Application in Food Products
The test method of the determination of preservative action in bratwurst sausage was used.
Treatments

| | |
|---|---|
| 1. Control (no treatment added) | Control |
| 2. LAE 0.2 g/kg | LAE |
| 3. LAE 0.2 g/kg + sodium citrate 3.0 g/kg | LAE + NaC |
| 4. LAE 0.2 g/kg + sodium hexametaphosphate 3.0 g/kg | LAE + NaP |

Sodium citrate was obtained at: Quimidroga, sodium hexametaphosphate at BK Giulini Chemie.

All concentrations in the above treatments relate to the amount of preservative compound per kg bratwurst sausage.

Microbiological Results

Figure 2:
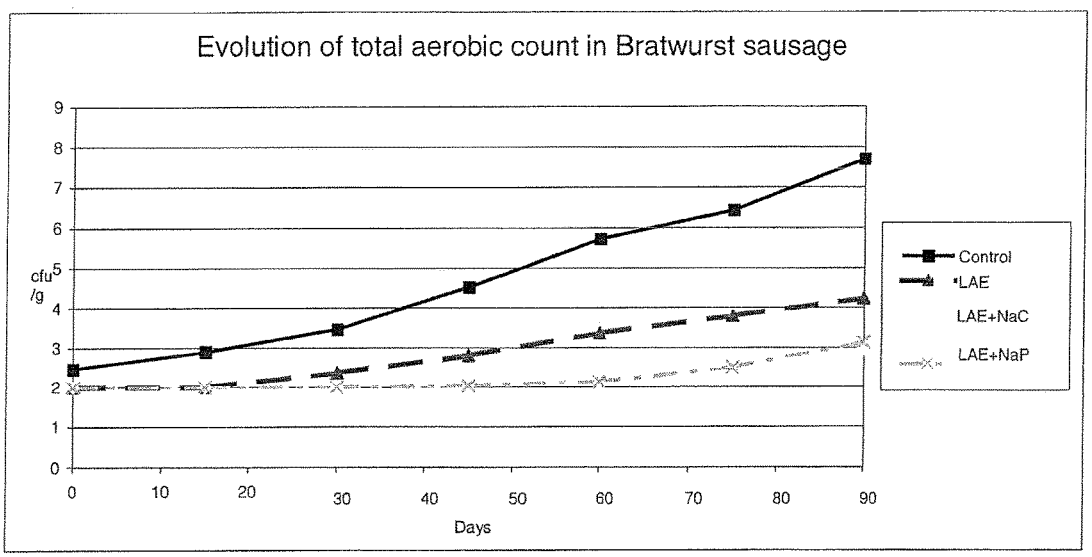

In table 3 and the corresponding FIG. 2 it is shown that at day 45 the control samples have a recount over 4 log cfu/g, however the samples treated with LAE have 2.8 log cfu/g and the samples treated with combinations of LAE with sodium citrate and sodium hexametaphosphate have 2.0 log cfu/g.

At day 75 the control samples are considered to be spoiled, samples treated with LAE have already a recount over 4 log cfu/g and if the samples are treated with the combinations of LAE with sodium citrate and sodium hexametaphosphate this recount is improved, 3 log cfu/g.

So, a treatment of LAE in combination with salts is even more effective than a treatment with LAE alone.

Over 90 days all the samples treated with LAE alone or in combination have a good color, appearance and color but in control samples a viscous liquid was observed in the surface of the bratwurst.

TABLE 3

Results for aerobic total count

| | Control | LAE | LAE + NaC | LAE + NaP | Days |
|---|---|---|---|---|---|
| 1 | 2.5 | 2.0 | 2.0 | 2.0 | 0 |
| 2 | 2.9 | 2.0 | 2.0 | 2.0 | |
| 3 | 2.0 | 2.0 | 2.0 | 2.0 | |
| mean | 2.4 | 2.0 | 2.0 | 2.0 | |
| 1 | 2.9 | 2.0 | 2.0 | 2.0 | 15 |
| 2 | 3.0 | 2.0 | 2.0 | 2.0 | |
| 3 | 2.8 | 2.0 | 2.0 | 2.0 | |
| mean | 2.9 | 2.0 | 2.0 | 2.0 | |
| 1 | 3.7 | 2.3 | 2.0 | 2.0 | 30 |
| 2 | 3.5 | 2.5 | 2.0 | 2.0 | |
| 3 | 3.2 | 2.3 | 2.0 | 2.0 | |
| mean | 3.5 | 2.4 | 2.0 | 2.0 | |
| 1 | 4.4 | 2.5 | 2.1 | 2.1 | 45 |
| 2 | 4.6 | 2.9 | 2.0 | 2.0 | |
| 3 | 4.6 | 3.0 | 2.0 | 2.0 | |
| mean | 4.5 | 2.8 | 2.0 | 2.0 | |
| 1 | 5.5 | 3.3 | 2.1 | 2.1 | 60 |
| 2 | 5.9 | 3.2 | 2.2 | 2.3 | |
| 3 | 5.8 | 3.6 | 2.0 | 2.0 | |
| mean | 5.7 | 3.4 | 2.1 | 2.1 | |
| 1 | 6.3 | 3.9 | 2.7 | 2.5 | 75 |
| 2 | 6.5 | 3.6 | 2.6 | 2.6 | |
| 3 | 6.5 | 3.9 | 2.4 | 2.4 | |
| mean | 6.4 | 3.8 | 2.6 | 2.5 | |
| 1 | 7.4 | 4.2 | 3.0 | 3.2 | 90 |
| 2 | 8.0 | 4.1 | 2.8 | 3.4 | |

TABLE 3-continued

Results for aerobic total count

| | Control | LAE | LAE + NaC | LAE + NaP | Days |
|---|---|---|---|---|---|
| 3 | 7.7 | 4.4 | 3.1 | 2.8 | |
| mean | 7.7 | 4.2 | 3.0 | 3.1 | |

The results expressed in log cfu/g
Physico-chemical Results

The evolution of the pH of the four treatments was analysed during the 90 days. No difference between the pH values in any of the treated and the control samples was observed. So, the addition of LAE combined with salts did not influence the pH characteristics of the bratwurst sausages.

Example 12

Combination with Salts of Organic/Inorganic Acids
Application in Cosmetic Products
As a test method the above method for the determination of preservative action in cosmetic products was chosen.
Bath Gels
The following composition of a formulation for a bath gel was prepared (in g):

| | |
|---|---|
| Sodium lauryl sulfate (sol. 27%) | 14.00 |
| Cocamidopropyl betaine | 6.00 |
| Disodium cocoamfoacetate | 6.00 |
| Lactic acid | 0.25 |
| Sodium chloride | 0.50 |
| Aqua | 100 c.s.p. |

This formulation is applied in bath gels.

The used products were obtained at the following sources: sodium lauryl sulfate: Cognis; cocamidopropyl betaine: Degussa; disodium cocoamfoacetate: Impex; lactic acid: Purac and sodium chloride: Panreac.

This formulation is completed with the different treatments and their capacity of preservation is evaluated against the formulation without LAE (control).

| | |
|---|---|
| 1. Control (no treatment added) | Control |
| 2. LAE 0.2 g/kg | LAE |
| 3. LAE 0.2 g/kg + sodium citrate 3.0 g/kg | LAE + NaC |
| 4. LAE 0.2 g/kg + sodium hexametaphosphate 3.0 g/kg | LAE + NaP |

Microbiological Results
The experimental data are provided in table 4.

TABLE 4

| | Microorganism | Control | LAE | LAE + NaC | LAE + NaP |
|---|---|---|---|---|---|
| 0 days | Aerobes | 6.6 | 6.2 | 6.3 | 6.3 |
| | Moulds | 4.7 | 4.5 | 4.6 | 4.7 |
| | Yeast | 4.9 | 4.3 | 4.7 | 4.5 |
| 7 days | Aerobes | 7.0 | 4.2 | 2.5 | 2.5 |
| | Moulds | 4.3 | 2.3 | <2.0 | <2.0 |
| | Yeast | 5.1 | 2.8 | <2.0 | <2.0 |
| 14 days | Aerobes | 7.7 | 3.0 | <2.0 | <2.0 |
| | Moulds | 3.9 | <2.0 | <2.0 | <2.0 |
| | Yeast | 5.4 | <2.0 | <2.0 | <2.0 |

The results are expressed in log cfu/g

No counts of aerobes, moulds and yeast were observed at day 28. According to the results of the study, if a bath gel is treated with the combinations of LAE with sodium citrate and sodium hexametaphosphate, it is effectively preserved.

A treatment of the bath gel with citrates or phosphates reduces the log of inoculated microorganisms by more than 2 log cfu/ml. The combined preservative has an even better efficacy as a preservative than LAE without salts.

Physico-chemical Results

The evolution of the pH of the four treatments was analysed during the 28 days. No difference between the pH values in any of the treated samples or control samples was observed. So, the addition of LAE combined with salts did not influence the pH characteristics of the bath gel.

Example 13

Combination of Cationic Surfactants with Another Ester Compound
Application in Food Products The test method of the determination of the preservative action and the concentration in chick peas was used.

Treatments

1. Control (no treatment added) BI
2. LAE 0.2 g/kg was added in soaking water LAE
3. LAE 0.2 g/kg + triethylcitrate 1.0 g/kg were added in soaking water LAE + tECit
4. LAE 0.2 g/kg + ethyl arginate 1.0 g/kg were added in soaking water LAE + EtAr Results of LAE Concentration In FIG. 3 and the table 5 the data expressed as % of initial concentration are displayed As can be observed from the figure and the data in the table, the hydrolysis of LAE reaches nearly 10% of the original dose after 24 hours.

On the other hand, this hydrolysis is delayed in the combination of LAE with triethyl citrate and with ethyl arginate. At 24 hours the initial dose is maintained for both treatment.

TABLE 5

Concentration data (HPLC method) expressed as % of initial dose

| | BI | LAE | LAE + tECit | LAE + EtAr | Hours |
|---|---|---|---|---|---|
| 1 | 0 | 100 | 100 | 100 | 0 |
| 2 | 0 | 100 | 99 | 101 | |
| 3 | 0 | 101 | 102 | 100 | |
| mean | 0 | 100 | 100 | 100 | |
| 1 | 0 | 100 | 102 | 101 | 4 |
| 2 | 0 | 101 | 99 | 100 | |
| 3 | 0 | 99 | 99 | 99 | |
| mean | 0 | 100 | 100 | 100 | |
| 1 | 0 | 97 | 100 | 100 | 8 |
| 2 | 0 | 98 | 100 | 99 | |
| 3 | 0 | 99 | 102 | 100 | |
| mean | 0 | 98 | 101 | 100 | |
| 1 | 0 | 95 | 100 | 101 | 16 |
| 2 | 0 | 96 | 99 | 98 | |
| 3 | 0 | 95 | 99 | 100 | |
| mean | 0 | 95 | 99 | 100 | |
| 1 | 0 | 93 | 99 | 101 | 24 |
| 2 | 0 | 92 | 98 | 99 | |
| 3 | 0 | 94 | 100 | 100 | |
| mean | 0 | 93 | 99 | 100 | |

Results of Aerobes in Chickpeas

The experimental data are provided in table 6. A graphical representation is displayed in FIG. 4.

Samples of soaked chickpeas treated with LAE, had counts slightly above 4.0 log cfu/g after 24 hours of soaking.

Control samples at the same time had 8.4 log cfu/g, which can be considered as being already spoiled.

In contrast, samples of chickpeas treated with LAE in combination with ethyl arginate or triethyl citrate had counts around 3.0 log cfu/g after 24 hours of soaking (1 log lower than with LAE).

After 24 hours samples of chickpeas treated with LAE mixed with ethyl arginate or LAE mixed with triethylcitrate were 1.0 log cfu/g below samples of chicken treated with LAE.

All treated samples had a nice and correct appearance at the end of the experiment.

Control samples even at 16 hours had arrived to 7.3 log cfu/g and the smell was very badly and the general appearance was not appealing.

TABLE 6

Results for aerobic total count

| | BI | LAE | LAE + tECit | LAE + EtAr | Hours |
|---|---|---|---|---|---|
| 1 | 2.0 | 2.0 | 2.0 | 2.0 | 0 |
| 2 | 2.0 | 2.0 | 2.0 | 2.0 | |
| 3 | 2.0 | 2.0 | 2.0 | 2.0 | |
| mean | 2.0 | 2.0 | 2.0 | 2.0 | |
| 1 | 2.9 | 2.0 | 2.0 | 2.0 | 4 |
| 2 | 3.4 | 2.0 | 2.0 | 2.0 | |
| 3 | 3.5 | 2.0 | 2.0 | 2.0 | |
| mean | 3.3 | 2.0 | 2.0 | 2.0 | |
| 1 | 4.5 | 2.7 | 2.0 | 2.4 | 8 |
| 2 | 4.8 | 2.6 | 2.1 | 2.3 | |
| 3 | 4.7 | 2.3 | 2.2 | 2.0 | |
| mean | 4.7 | 2.5 | 2.1 | 2.2 | |
| 1 | 7.5 | 3.9 | 2.1 | 2.1 | 16 |
| 2 | 6.9 | 3.6 | 2.5 | 2.4 | |
| 3 | 7.4 | 3.9 | 2.6 | 2.4 | |
| mean | 7.3 | 3.8 | 2.4 | 2.3 | |
| 1 | 8.5 | 4.2 | 3.0 | 2.9 | 24 |
| 2 | 8.3 | 4.5 | 3.2 | 3.1 | |
| 3 | 8.3 | 4.1 | 3.4 | 2.6 | |
| mean | 8.4 | 4.3 | 3.2 | 2.9 | |

Results expressed in log cfu/g

Example 14

Combination of Cationic Surfactants with Cationic Molecules
Application in Food Products As a test method the determination of preservative action in chicken breast was chosen.

Treatments

1. Control (no treatment added): BI
2. LAE 0.2 g/kg: LAE
3. LAE 0.2 g/kg + ethyl arginate 1.0 g/kg: LAE + EtAr Ethyl arginate was obtained at Aldrich.

All concentrations in the above treatments relate to the amount of preservative compound per kg meat.

Results

The results are shown in the next table 7. A graphical representation is displayed in FIG. 5.

Samples of cooked chicken treated with LAE, have counts below 4.0 log cfu/g for 5 weeks.

Control samples at the same time have 6.9 log cfu/g which can be considered already spoiled.

In contrast, samples of chicken treated with LAE mixed with ethyl arginate have counts below 4.0 log cfu/g even at 8 weeks (3 weeks later than with LAE).

At 8 weeks samples of chicken treated with LAE mixed with ethyl arginate are 1.5 log cfu/g below samples of chicken treated with LAE.

All treated samples have a nice and correct appearance at the end of the experiment.

Control samples at 8 weeks have arrived to 8.5 log cfu/g smell very badly and the presence of viscous liquid is detected.

TABLE 7

Results of aerobic total count

|  | BI | LAE | LAE + EtAr | Days |
|---|---|---|---|---|
| 1 | 2.0 | 2.0 | 2.0 | 0 |
| 2 | 2.0 | 2.0 | 2.0 |  |
| 3 | 2.0 | 2.0 | 2.0 |  |
| mean | 2.0 | 2.0 | 2.0 |  |
| 1 | 2.1 | 2.0 | 2.0 | 7 |
| 2 | 2.5 | 2.0 | 2.0 |  |
| 3 | 2.9 | 2.0 | 2.0 |  |
| mean | 2.5 | 2.0 | 2.0 |  |
| 1 | 3.8 | 2.2 | 2.0 | 14 |
| 2 | 3.6 | 2.6 | 2.0 |  |
| 3 | 3.2 | 2.2 | 2.0 |  |
| mean | 3.5 | 2.3 | 2.0 |  |
| 1 | 4.8 | 3.0 | 2.1 | 21 |
| 2 | 4.5 | 2.8 | 2.0 |  |
| 3 | 4.9 | 3.0 | 2.0 |  |
| mean | 4.7 | 2.9 | 2.0 |  |
| 1 | 5.8 | 3.4 | 2.5 | 28 |
| 2 | 6.2 | 3.2 | 2.1 |  |
| 3 | 5.9 | 3.5 | 2.4 |  |
| mean | 6.0 | 3.4 | 2.3 |  |
| 1 | 6.9 | 3.6 | 2.5 | 35 |
| 2 | 7.2 | 3.8 | 2.6 |  |
| 3 | 6.6 | 3.9 | 2.4 |  |
| mean | 6.9 | 3.8 | 2.5 |  |
| 1 | 7.9 | 4.0 | 3.0 | 42 |
| 2 | 8.5 | 4.0 | 3.4 |  |
| 3 | 8.1 | 4.1 | 2.8 |  |
| mean | 8.2 | 4.0 | 3.1 |  |
| 1 | 8.6 | 5.3 | 3.2 | 49 |
| 2 | 8.5 | 4.9 | 3.5 |  |
| 3 | 8.1 | 5.0 | 3.6 |  |
| mean | 8.4 | 5.1 | 3.4 |  |
| 1 | 8.3 | 5.2 | 4.0 | 56 |
| 2 | 8.6 | 5.6 | 4.0 |  |
| 3 | 8.6 | 6.0 | 3.7 |  |
| mean | 8.5 | 5.6 | 3.9 |  |

Results expressed in log cfu/g

Example 15

Combination of Cationic Surfactants with Cationic Molecules
Application in Cosmetic Products As a test method the above method for the determination of preservative action in cosmetic products was chosen.

Bath Gels

The following composition of a formulation for a bath gel was prepared (in g):

| Sodium lauryl sulfate (sol. 27%) | 14.00 |
|---|---|
| Cocamidopropyl betaine | 6.00 |
| Disodium cocoamfoacetate | 6.00 |
| Lactic acid | 0.25 |
| Sodium chloride | 0.50 |
| Aqua | 100 c.s.p. |

The used products were obtained at the following sources: sodium lauryl sulfate: Cognis; cocamidopropyl betaine: Degussa; disodium cocoamfoacetate: Impex; lactic acid: Purac and sodium chloride: Panreac.

This formulation is applied in bath gels to obtain an aqueous solution.

This formulation was completed with the addition of different preservatives and their capacity of preservation was evaluated against the formulation without LAE (control).

| 1. Control (no treatment added) | BI |
|---|---|
| 2. LAE 0.2 g/kg | LAE |
| 3. LAE 0.2 g/kg + ethyl arginate 1.0 g/kg | LAE + EtAr |

The indicated concentration is in g per kg of the formulation.

The results are shown in next table 8.

TABLE 8

|  | Microorganism | BI | LAE | LAE + EtAr |
|---|---|---|---|---|
| 0 days | Aerobes | 6.6 | 6.1 | 6.3 |
|  | Moulds | 4.0 | 4.1 | 4.2 |
|  | Yeast | 4.5 | 4.3 | 4.5 |
| 7 days | Aerobes | 7.4 | 3.0 | 2.5 |
|  | Moulds | 3.1 | <2.0 | <2.0 |
|  | Yeast | 4.3 | 3.3 | 2.1 |
| 14 days | Aerobes | 7.9 | 2.6 | <2.0 |
|  | Moulds | 3.4 | <2.0 | <2.0 |
|  | Yeast | 4.6 | 2.6 | <2.0 |

The results are provided in log cfu/g

At 28 days no increase was detected compared with the count after 14 days.

In conclusion, it is clear that a bath gel treated with a combination of LAE with ethyl arginate is effectively preserved.

The addition of ethyl arginate increases log reductions of inoculated microorganisms by more than 1 log cfu/mL.

Preservation with LAE mixed with ethyl arginate is improved

Example 16

Encapsulation of Cationic Surfactants
Application in Food Products
Cooked Chicken Breast
Treatments

| 1. Control (no treatment added) | BI |
|---|---|
| 2. LAE 0.2 g/kg | LAE |
| 3. LAE encapsulated with palm oil 0.20 g of LAE/kg | LAE + palm |
| 4. LAE emulsion with soya oil 0.20 g of LAE/kg | LAE + emSy |
| 5. LAE in lecithin 0.20 g of LAE/kg | LAE + leci |
| 6. LAE with tween 20 at 0.20 g of LAE/kg | LAE + t20 |

Results

The experimental data are provided in table 9. A graphical representation is displayed in FIG. 6.

Samples of cooked chicken treated with LAE, have counts below 4.0 log cfu/g for 5 weeks.

Control samples at the same time have 6.9 log cfu/g which can be considered already spoiled.

In contrast, samples of chicken treated with LAE encapsulated with different technologies have counts below 4.0 log cfu/g even at 8 weeks (3 weeks later than with LAE).

All treated samples have a nice and correct appearance at the end of the experiment.

Control samples at 8 weeks have arrived to 8.5 log cfu/g smell very badly and the presence of viscous liquid is detected.

TABLE 9

Results for aerobic total count

|  | BI | LAE | LAE + palm | LAE + emSy | LAE + leci | LAE + t20 | Days |
|---|---|---|---|---|---|---|---|
| 1 | 2.0 | 2.0 | 2.0 | 2.0 | 2.0 | 2.0 | 0 |
| 2 | 2.0 | 2.0 | 2.0 | 2.0 | 2.0 | 2.0 |  |
| 3 | 2.0 | 2.0 | 2.0 | 2.0 | 2.0 | 2.0 |  |
| mean | 2.0 | 2.0 | 2.0 | 2.0 | 2.0 | 2.0 |  |
| 1 | 2.6 | 2.0 | 2.0 | 2.0 | 2.0 | 2.0 | 7 |
| 2 | 2.5 | 2.0 | 2.0 | 2.0 | 2.0 | 2.0 |  |
| 3 | 2.5 | 2.0 | 2.0 | 2.0 | 2.0 | 2.0 |  |
| mean | 2.5 | 2.0 | 2.0 | 2.0 | 2.0 | 2.0 |  |
| 1 | 3.3 | 2.4 | 2.0 | 2.0 | 2.0 | 2.0 | 14 |
| 2 | 3.2 | 2.2 | 2.0 | 2.0 | 2.0 | 2.0 |  |
| 3 | 3.5 | 2.1 | 2.0 | 2.0 | 2.0 | 2.0 |  |
| mean | 3.3 | 2.2 | 2.0 | 2.0 | 2.0 | 2.0 |  |
| 1 | 4.2 | 2.7 | 2.2 | 2.1 | 2.1 | 2.1 | 21 |
| 2 | 4.0 | 2.6 | 2.0 | 2.4 | 2.0 | 2.2 |  |
| 3 | 4.6 | 3.1 | 2.0 | 2.1 | 2.0 | 2.4 |  |
| mean | 4.3 | 2.8 | 2.1 | 2.2 | 2.0 | 2.2 |  |
| 1 | 6.0 | 2.9 | 2.5 | 2.0 | 2.5 | 2.5 | 28 |
| 2 | 5.6 | 3.2 | 2.1 | 2.6 | 2.3 | 2.8 |  |
| 3 | 6.2 | 3.4 | 2.3 | 2.5 | 2.3 | 2.2 |  |
| mean | 5.9 | 3.2 | 2.3 | 2.4 | 2.4 | 2.5 |  |
| 1 | 6.9 | 3.4 | 2.0 | 2.9 | 2.0 | 2.3 | 35 |
| 2 | 6.5 | 3.7 | 2.6 | 2.5 | 2.5 | 2.5 |  |
| 3 | 7.2 | 3.7 | 2.6 | 2.5 | 2.6 | 2.3 |  |
| mean | 6.9 | 3.6 | 2.4 | 2.6 | 2.4 | 2.4 |  |
| 1 | 8.2 | 4.5 | 3.0 | 3.2 | 2.3 | 2.6 | 42 |
| 2 | 7.6 | 4.3 | 2.8 | 3.4 | 2.5 | 2.5 |  |
| 3 | 7.8 | 4.1 | 3.0 | 3.6 | 2.5 | 2.3 |  |
| mean | 7.9 | 4.3 | 2.9 | 3.4 | 2.4 | 2.5 |  |
| 1 | 8.6 | 5.0 | 3.3 | 3.5 | 3.2 | 3.0 | 49 |
| 2 | 8.5 | 4.7 | 3.0 | 3.6 | 3.0 | 3.0 |  |
| 3 | 8.6 | 5.1 | 3.4 | 3.6 | 3.4 | 2.9 |  |
| mean | 8.6 | 4.9 | 3.2 | 3.6 | 3.2 | 3.0 |  |
| 1 | 8.3 | 5.6 | 3.6 | 4.0 | 3.5 | 3.2 | 56 |
| 2 | 8.5 | 5.4 | 3.8 | 4.2 | 3.6 | 3.2 |  |
| 3 | 8.6 | 5.6 | 3.6 | 3.8 | 3.3 | 3.6 |  |
| mean | 8.5 | 5.5 | 3.7 | 4.0 | 3.5 | 3.3 |  |

Results expressed in log cfu/g

Example 17

Encapsulation of Cationic Surfactants
Application in Cosmetic Products
Oil in Water Emulsion with an Ionic Emulsifier The composition of an oil-in-water emulsion with an ionic emulsifier, used as cosmetic formulation, is (in g):

| Stearic acid | 1.90 |
| Glyceryl stearate S.E. | 2.80 |
| Cetyl alcohol | 1.80 |
| Paraffinum | 3.10 |
| Isopropyl myristate | 3.00 |
| Caprylic-caproic triglycerides | 3.00 |
| Dimethicone | 0.40 |
| Propylene glycol | 3.00 |
| Cellulose gum | 0.50 |
| Triethanolamine | 1.05 |
| Aqua | 100 c.s.p. |

The used products were obtained at the following sources: stearic acid: Uniqema; glyceryl stearate: Degussa; cetyl alcohol: Degussa; paraffinum: Impex; isopropyl myristate: Degussa; caprylic-caproic triglycerides: Degussa; dimethicone: Degussa; propylene glycol: Quimidroga; cellulose gum: Hercules and triethanolamine: Quimidroga.

The preparation of the oil in water emulsion with an ionic emulsifier was as follows: the oil ingredients (stearic acid, glyceryl stearate S.E., cetyl alcohol, paraffinum, isopropyl myristate, caprylic-caproic triglycerides, dimethicone) were mixed together and heated at 75° C. The water phase (consisting of propylene glycol, cellulose gum, triethanolamine and aqua) was also heated to 75° C.

The oil phase was added to the water phase under stirring of approximately 5000 rpm by Ultraturrax. The emulgation was completed in 2 minutes. The emulsion was cooled fast to room temperature while stirring at a low speed of 20 rpm. Triethanolamine was added to adjust the pH to 6-7.

This formulation is completed with the different treatments and their capacity of preservation is evaluated against the formulation without LAE (control).

| 1. Control (no treatment added) | BI |
| 2. LAE 0.2 g/kg | LAE |
| 3. LAE encapsulated with palm oil 0.20 g of LAE/kg | LAE + palm |
| 4. LAE emulsion with soybean oil 0.20 g of LAE/kg | LAE + emSy |
| 5. LAE in lecithin at 0.20 g of LAE/kg | LAE + leci |
| 6. LAE with tween 20 at 0.20 g of LAE/kg | LAE + t20 |

The experimental data are provided in table 10.

TABLE 10

|  | Micro-organism | BI | LAE | LAE + palm | LAE + emSy | LAE + leci | LAE + t20 |
|---|---|---|---|---|---|---|---|
| 0 days | Aerobes | 6.4 | 6.1 | 6.1 | 6.3 | 6.2 | 6.0 |
|  | Moulds | 4.4 | 4.1 | 4.2 | 4.1 | 4.3 | 4.3 |
|  | Yeast | 5.5 | 5.3 | 5.5 | 5.2 | 5.4 | 5.3 |
| 7 days | Aerobes | 7.2 | 4.0 | 2.9 | 2.5 | 2.4 | 2.7 |
|  | Moulds | 4.1 | 2.9 | <2.0 | <2.0 | <2.0 | <2.0 |
|  | Yeast | 5.9 | 3.8 | 2.0 | <2.0 | 2.5 | 3.1 |
| 14 days | Aerobes | 8.0 | 2.9 | <2.0 | <2.0 | <2.0 | <2.0 |
|  | Moulds | 5.9 | <2.0 | <2.0 | <2.0 | <2.0 | <2.0 |
|  | Yeast | 6.6 | 2.5 | <2.0 | <2.0 | <2.0 | <2.0 |

The results are in log cfu/g

At 28 days no increase has been detected from the 14 days' count.

Therefore, is clear that oil in water emulsion with an ionic emulsifier treated with LAE at 0.2 g/kg (LAE), LAE encapsulated with palm oil at 0.20 g of LAE/kg (LAE+palm), LAE emulsion with soybean oil at 0.20 g of LAE /kg (LAE+emSy), LAE in lecithin at 0.20 g of LAE/kg (LAE+leci) and LAE with tween 20 at 0.20 g of LAE/kg (LAE+t20) are effectively preserved.

Treatments of covered/encapsulated LAE (LAE encapsulated with palm oil at 0.20 g of LAE/kg (LAE+palm), LAE emulsion with soya oil at 0.20 g of LAE/kg (LAE+emSy), LAE in lecithin at 0.20 g of LAE/kg (LAE+leci) and LAE with tween 20 at 0.20 g of LAE/kg (LAE+t20)) increase log reductions of inoculated micro organisms by more than 1 log cfu/mL.

Therefore treatments of the covered/encapsulated LAE lead to improved results compared to LAE.

Example 18

Encapsulation of Cationic Surfactants and Combination with Salt and Ester Compounds
Application in Food Products
Cooked Chicken Breast
Treatments

| | |
|---|---|
| 1. Control (no treatment added) | BI |
| 2. LAE at 0.2 g/kg | LAE |
| 3. LAE acetate in lecithin at 0.2 g of LAE/kg + ethyl arginate at 1.0 g/kg + sodium citrate at 3.0 g/kg + triethylcitrate at 1.0 g/kg | LAE + SYN |

The results are shown in the next table 11.

TABLE 11

| | BI | LAE | LAE + SYN | Days |
|---|---|---|---|---|
| 1 | 2.0 | 2.0 | 2.0 | 0 |
| 2 | 2.0 | 2.0 | 2.0 | |
| 3 | 2.0 | 2.0 | 2.0 | |
| Mean | 2.0 | 2.0 | 2.0 | |
| 1 | 2.5 | 2.0 | 2.0 | 7 |
| 2 | 2.3 | 2.0 | 2.0 | |
| 3 | 2.8 | 2.0 | 2.0 | |
| Mean | 2.5 | 2.0 | 2.0 | |
| 1 | 3.7 | 2.2 | 2.0 | 14 |
| 2 | 3.5 | 2.6 | 2.0 | |
| 3 | 3.4 | 2.4 | 2.0 | |
| Mean | 3.5 | 2.4 | 2.0 | |
| 1 | 4.5 | 3.0 | 2.0 | 21 |
| 2 | 4.5 | 2.7 | 2.0 | |
| 3 | 5.0 | 3.1 | 2.0 | |
| Mean | 4.7 | 2.9 | 2.0 | |
| 1 | 6.3 | 3.3 | 2.0 | 28 |
| 2 | 5.9 | 3.4 | 2.0 | |
| 3 | 6.1 | 3.5 | 2.0 | |
| Mean | 6.1 | 3.4 | 2.0 | |
| 1 | 7.0 | 3.6 | 2.0 | 35 |
| 2 | 7.3 | 3.7 | 2.0 | |
| 3 | 6.9 | 3.7 | 2.0 | |
| Mean | 7.1 | 3.7 | 2.0 | |
| 1 | 7.9 | 4.3 | 2.0 | 42 |
| 2 | 8.4 | 4.0 | 2.0 | |
| 3 | 8.3 | 3.9 | 2.2 | |
| Mean | 8.2 | 4.1 | 2.1 | |
| 1 | 8.1 | 5.3 | 2.1 | 49 |
| 2 | 8.4 | 5.0 | 2.0 | |
| 3 | 8.5 | 5.2 | 2.0 | |
| Mean | 8.3 | 5.2 | 2.0 | |
| 1 | 8.7 | 5.8 | 2.0 | 56 |
| 2 | 8.4 | 5.4 | 2.1 | |
| 3 | 8.6 | 5.9 | 2.3 | |
| Mean | 8.6 | 5.7 | 2.1 | |

Results expressed in log cfu/g
Samples of cooked chicken treated with LAE, had counts below 4.0 log cfu/g for 5 weeks.
Control samples at the same time had 7.1 log cfu/g, which can be considered already spoiled.
In contrast, samples of chicken treated with LAE+SYN had counts below 2.5 log cfu/g even at 8 weeks.
At 8 weeks samples of chicken treated with LAE+SYN were 3.5 log cfu/g below samples of chicken treated with LAE.
All treated samples had a nice and correct appearance at the end of the experiment.
Control samples at 8 weeks had arrived to 8.6 log cfu/g. They smelt very badly and the presence of viscous liquid was detected.

Example 19

Application in Cosmetic Products
As a test method the above method for the determination of preservative action in cosmetic products was chosen.
Bath Gels
The following composition of a formulation for a bath gel was prepared (in g):

| | |
|---|---|
| Sodium lauryl sulfate (sol. 27%) | 14.00 |
| Cocamidopropyl betaine | 6.00 |
| Disodium cocoamfoacetate | 6.00 |
| Lactic acid | 0.25 |
| Sodium chloride | 0.50 |
| Aqua | 100 c.s.p. |

The used products were obtained at the following sources: sodium lauryl sulfate: Cognis; cocamidopropyl betaine: Degussa; disodium cocoamfoacetate: Impex; lactic acid: Purac and sodium chloride: Panreac.
This formulation is applied in bath gels to obtain an aqueous solution.
This formulation was completed with the addition of different preservatives and their capacity of preservation was evaluated against the formulation without LAE (control).

| | |
|---|---|
| 1. Control (no treatment added) | BI |
| 2. LAE at 0.2 g/kg | LAE |
| 3. LAE acetate in lecithin at 0.2 g of LAE/kg + ethyl arginate at 1.0 g/kg + sodium citrate at 3.0 g/kg + triethylcitrate at 1.0 g/kg | LAE + SYN |

The experimental data are provided in table 12. A graphical representation is displayed in FIG. 7.

TABLE 12

| | Micro organism | BI | LAE | LAE + SYN |
|---|---|---|---|---|
| 0 days | Aerobes | 6.3 | 6.0 | 6.1 |
| | Moulds | 4.3 | 4.1 | 4.3 |
| | Yeast | 4.1 | 4.5 | 4.5 |
| 7 days | Aerobes | 7.2 | 3.3 | <2.0 |
| | Moulds | 3.5 | 2.0 | <2.0 |
| | Yeast | 4.8 | 3.5 | <2.0 |
| 14 days | Aerobes | 8.2 | 2.9 | <2.0 |
| | Moulds | 3.8 | <2.0 | <2.0 |
| | Yeast | 5.4 | 2.3 | <2.0 |

Results in log cfu/g
At 28 days no increase has been detected from the 14 days' count.
Therefore, is clear that bath gel treated with LAE+SYN is effectively preserved because:
 More than 2.0 logarithm reduction from the initial calculated bacteria's count is reached at 14 days and no increase from the 14 days' count at 28 days is detected
 No increase from the initial calculated count of yeast and moulds is observed.
LAE+SYN increases log reductions of inoculated micro organisms by more than 1 log cfu/mL.
Preservation with LAE+SYN is improved compared to LAE alone.

The invention claimed is:
1. A preservative system comprising a cationic surfactant, of the formula:

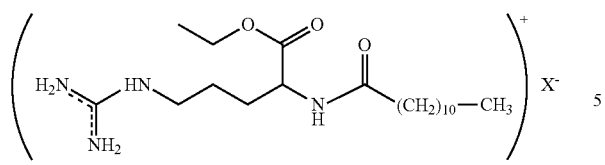

wherein X⁻ is an anion derived from an acid selected from the group consisting of lactic acid and glutamic acid.

2. A preservative system comprising:
(a) a cationic surfactant, of the formula:

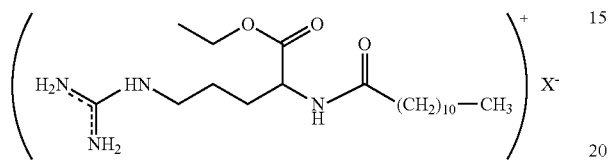

wherein X⁻ is an anion derived from organic or inorganic acids, and
(b) at least one salt selected from the group consisting of sodium citrate, sodium glutamate, sodium fumarate, sodium gluconate, sodium laurate, sodium lactate, sodium hexametaphosphate, sodium tertiary butyl hydroquinonate, sodium propylparabenate, glucosamine hydrochloride and ethanolamine hydrochloride, and combinations thereof, excluding salts of sorbic acid.

3. A preservative system comprising a cationic surfactant, of the formula:

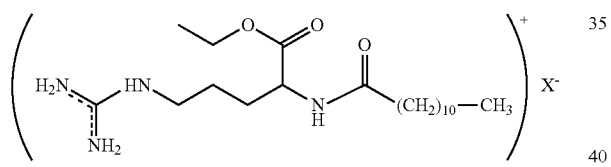

wherein X⁻ is an anion derived from organic or inorganic acids, and wherein the cationic surfactant is in an encapsulated form.

4. The preservative system of claim 3, wherein the encapsulated form is an oil-in-water emulsion.

5. The preservative system of claim 4, wherein the oil is selected from the group consisting of palm oil having a melt point of 35-80° C., soy bean oil, and sunflower oil.

6. The preservative system of claim 1, further comprising a preservative composition including:
(a) a cationic surfactant, the surfactant comprising the condensation product of fatty acids and esterified dibasic amino acids, wherein the surfactant has the formula:

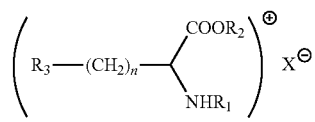

where:
X⁻ is selected from the group consisting of Br⁻, CL⁻, and HSO₄⁻,
R₁: is a straight alkyl chain of a saturated fatty acid or a hydroxy acid having 8 to 14 carbon atoms linked to an α-amino group via an amide bond;
R₂: is a straight or branched alkyl chain having from 1 to 18 carbon atoms or is aromatic;
R₃ is selected from the group consisting of : —NH₃,

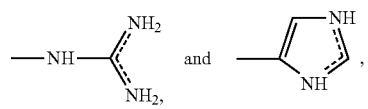

and n is from 0 to 4, and
(b) at least one salt of an organic or inorganic acid, excluding salts of sorbic acid.

7. A preservative system comprising a cationic surfactant, of the formula:

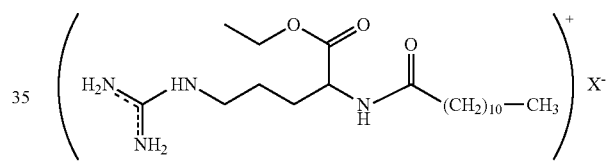

wherein X⁻ is an anion derived from organic or inorganic acids and wherein the carionic surfactant is an encapsulated form in which the cationic surfactant is coated with a coating agent selected from the group consisting of vegetable oils, animal oils, mineral oils, vegetable fats, animal fats, mineral fats, vegetable biopolymers, animal biopolymers, lecithin, and cyclodextrins, and combinations thereof.

8. The preservative system of claim 7, wherein the coating agent is applied with an encapsulation technique based on physical methods selected from the group consisting of spray chilling, spray drying, rotary disk atomization, fluid bed coating, stationary nozzle co-extrusion, centrifugal head co-extrusion, submerged nozzle extrusion and pan coating.

* * * * *